United States Patent [19]

Kremer

[11] Patent Number: 5,300,688

[45] Date of Patent: Apr. 5, 1994

[54] METHOD FOR MAKING HYDRAZIDE OR HYDRAZINE COMPOUNDS

[75] Inventor: Kenneth A. M. Kremer, Lawrenceville, N.J.

[73] Assignee: American Cyanamid Company, Wayne, N.J.

[21] Appl. No.: 976,764

[22] Filed: Nov. 16, 1992

[51] Int. Cl.$^5$ ................ C07C 241/02; C07C 241/04
[52] U.S. Cl. .................................. 564/149; 564/464
[58] Field of Search ........................... 564/149, 464

[56] References Cited

U.S. PATENT DOCUMENTS

| | | | |
|---|---|---|---|
| 2,917,545 | 12/1959 | Lum et al. | 564/464 |
| 3,956,366 | 5/1976 | Sheppard et al. | 560/159 |
| 3,976,756 | 8/1976 | Wojtowicz | 564/464 |
| 4,435,600 | 3/1984 | Hasegawa et al. | 564/464 |
| 4,857,550 | 8/1989 | Kameswaran et al. | 514/522 |
| 4,985,461 | 1/1991 | Hsu et al. | 514/615 |

*Primary Examiner*—Allen J. Robinson
*Assistant Examiner*—Deborah Lambkin
*Attorney, Agent, or Firm*—Michael P. Morris

[57] ABSTRACT

This invention relates to the preparation of hydrazide or hydrazine compounds. More particularly, this invention relates to an efficient method for the preparation of substituted hydrazides, hydrazines, and intermediates therefor, from urea starting products. Such hydrazide and hydrazine compounds are useful as insecticides.

15 Claims, No Drawings

METHOD FOR MAKING HYDRAZIDE OR HYDRAZINE COMPOUNDS

This invention relates to the preparation of hydrazide or hydrazine compounds. More particularly, this invention relates to an efficient method for the preparation of substituted hydrazides, hydrazines, and intermediates therefor, from urea starting products. Such hydrazide and hydrazine compounds are useful as insecticides.

BACKGROUND OF THE INVENTION

Ammonia and its derivatives are highly useful basic compounds which have many known uses. The family of ammonia compounds, for example, amines, amides, ureas, hydrazines, hydrazides, hydrazones, amidrazones, semicarbazides and semicarbazones, are useful in a variety of organic syntheses. The preparation of such basic ammonia compounds and their derivatives, however, is often costly and difficult, requiring many steps (See, e.g., U.S. Pat. No. 3,956,366).

Among these ammonia derivatives, hydrazide and hydrazine compounds are particularly useful as reducing agents in organic syntheses. However, the high cost of producing reagent quality hydrazides and hydrazines has reduced their practical utility in organic synthesis, such as in the production of acylated hydrazides or hydrazines. Such compounds have demonstrated useful insecticidal activity (See, e.g., U.S. Pat. No. 4,985,461, Japanese patent applications JP-091048 and JP-020216, and German patent application DE 3228631).

Efforts have been made to prepare such useful hydrazides, hydrazines, and substituted derivatives thereof, at low cost and in high yield without much success (see, e.g., U.S. Pat. Nos. 4,310,696, 4,435,600 and 4,954,655). The processes referred to in the above-listed patents are expensive, time consuming, and labor intensive.

There remains a need for a simple, low cost method to prepare hydrazide or hydrazine compounds so that their beneficial properties can be made readily available to the public.

It is therefore an object of this invention to provide a process for the preparation of hydrazide or hydrazine compounds from readily available urea compounds.

Yet another object of the invention is to provide a more efficient process for preparation of substituted hydrazide or hydrazine compounds.

Another object of the invention is to provide a controlled method for the monoacylation and diacylation of urea compounds.

These and other objects of the invention will become apparent in the course of the detailed description of the invention which follows.

SUMMARY OF THE INVENTION

This invention relates to the preparation of hydrazide or hydrazine compounds. More particularly, this invention relates to a novel method for the preparation of substituted hydrazides, hydrazines, and intermediates therefor, from urea starting products. Such compounds are useful as insecticides.

DETAILED DESCRIPTION OF THE INVENTION

This invention provides a novel and simple method for the preparation of hydrazide or hydrazine compounds. Such compounds have demonstrated useful pesticidal activity (See, e.g., U.S. Pat. No. 4,985,461, Japanese patent applications JP-091048 and JP-020216, and German patent application DE 3228631).

In particular, substituted hydrazide or hydrazine compounds are useful as insecticidal agents and are particularly effective when used for the control of lepidopterous insects. They are extremely potent insect stomach poisons and systemic insecticidal agents, effective for controlling a variety of insects including Acarina, Lepidoptera, Homoptera, Orthoptera, Coleoptera and Diptera, and are likewise effective for protecting a variety of crops from insect attack. These compounds have also been found to have some activity as contact insecticides.

We have discovered a convenient method for the preparation of such useful hydrazide or hydrazine compounds from urea starting products using the Schotten-Baumann technique. The method involves the halogenation of urea starting products to produce halogenated hydrazine or hydrazide intermediates as a dilute aqueous solution. Such crude intermediates are then directly converted into useful hydrazide and hydrazine compounds.

The high yield production of such useful compounds in a continuous method from a crude, dilute hydrazine-containing intermediate aqueous stream was unexpected. Such a process has clear advantages over prior art batch processes and processes requiring evaporation or purification of intermediate compounds in order to produce a satisfactory yield of a useful hydrazide or hydrazine end product.

In a preferred process of the invention, hydrazide and hydrazine compounds of the following general formulae, e.g., as referred to in U.S. Pat. No. 4,887,550, are prepared:

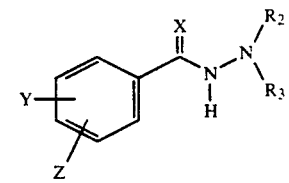

or

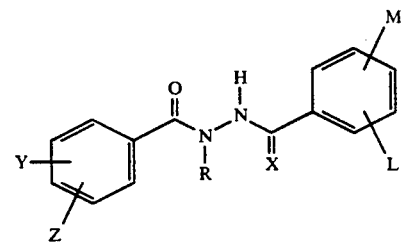

wherein R is $C_2-C_6$ alkyl; Y, Z, L and M are each independently H, $C_1-C_3$ alkyl, methoxy, ethoxy, F, Cl, Br, I, CN, nitro, $CF_3$, $CH_3S$, $R_1CF_2-$, 1,1-difluoro-2,2-dichloroetoxy, acetamido or sulfamoyl, and when taken together, Y and Z may form a ring in which YZ is pyridyl, furyl, pyrrolyl or thiophenyl, or represented by the structure:

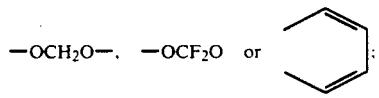

and when taken together, L and M may form a ring in which LM is pyridyl, furyl, pyrrolyl or thiophenyl, or represented by the structure:

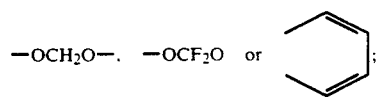

X is S or O; $R_1$ is H, F, $CHF_2$ or $CF_3$; and $R_2$ and $R_3$ are each independently hydrogen, $C_1$-$C_6$ alkyl, $C_5$-$C_6$ cycloalkyl or aryoyl.

The most preferred process produces compounds wherein R = t-butyl, and X is O (See Jensen et al., *Acta. Chem. Scand.*, 15, page 1109 (1961)).

Substituted diacylated hydrazines prepared by the process of the invention may be symmetrical or asymmetrical. Symmetrical analogs, in which the substituents on both aromatic rings are identical, can be prepared in one step by reacting a hydrazine-containing dilute aqueous solution, e.g., alkylhydrazine hydrochloride, with at least about two equivalents of the appropriate acid halide in a two-phase system consisting of aqueous base, such as NaOH, $Na_2CO_3$ or KOH, and a first aprotic organic solvent, usually methylene chloride, anhydrous tetrahydrofuran, acetone or ether. This simple procedure allows for the rapid introduction of a variety of substituents into the final products.

For asymmetrical analogs, the Schotten-Baumann reaction may be carried out with about one equivalent of the appropriate acid halide to produce an intermediate hydrazide, which may then be directly acylated with a second mole of another acid chloride to give the asymmetrical compounds.

In a most preferred embodiment, this invention relates to the preparation of mono and dibenzoyl hydrazides and hydrazines from urea starting products. Such compounds may be prepared by the reaction set forth below:

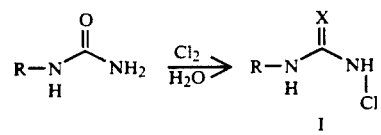

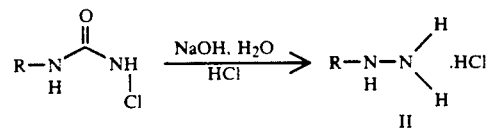

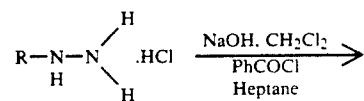

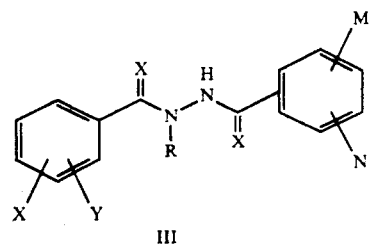

III

In this most preferred acylation process of the invention, a halogen compound, e.g., chlorine, is added to a chilled aqueous alkylurea slurry to produce a halogenated alkylurea (I). The halogenated alkylurea, either as a slurry or as a solid after drying, is reacted with a dilute solution of an aqueous base, preferably $Na_2CO_3$ or NaOH, and stirred. When the reaction is complete, the solid by-products are filtered off. The filtrate is then acidified with a concentrated acid, preferably HCl, producing alkylhydrazine hydrohalide as a dilute, e.g., between about 0.5% and 10%, preferably between about 2% and 4%, aqueous solution (II) (referred to hereinafter as a "hydrazine-containing dilute aqueous solution").

In the next, but continuous, step of the most preferred process of the invention, an aqueous base, typically about two to about six molar equivalents of sodium carbonate or sodium hydroxide per equivalent of hydrazine-containing dilute aqueous solution, a chlorinated hydrocarbon, such as methylene chloride, or other inert organic solvent, and two molar equivalents of an appropriate acid halide, such as benzoyl chloride or other acid chlorides such as acetyl chloride or benzenesulfonyl chloride, are added to the crude hydrazine-containing dilute aqueous solution at room temperature. After allowing the reaction to proceed to completion, the organic phase is drained off. A second solvent, such as heptane or other inert organic solvent, is then added to the organic phase to produce a high yield of a diacylated hydrazine with good purity (III). In a like manner, monoacylated hydrazides may be prepared by reacting one molar equivalent of the hydrazine-containing dilute aqueous solution with one molar equivalent of an acid halide in the presence of one molar equivalent of NaOH as set forth below.

-continued

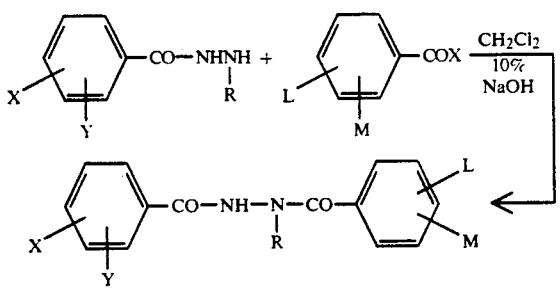

In order to facilitate a further understanding of the invention, the following examples are presented primarily for the purpose of illustrating certain more specific details thereof. The invention is not to be deemed limited thereby except as defined in the claims.

EXAMPLE 1

Preparation of N-chloro-t-butylurea from t-butylurea

To a stirring slurry of 8.2 g (0.0706 mole) of t-butylurea in 110 mL of water at 0°–5° C. is charged 6.0 g (0.085 mole) of chlorine over 20 minutes. The resulting slurry is stirred for 1 hour at 0°–10° C. and then filtered, water washed and dried. The solid product is used directly in Example 2.

Alternatively, the solid isolation can be avoided by using the slurry of N-chloro-t-butylurea directly without filtration. To the aqueous slurry from above is added 25.4 g of NaOH (50% 0.318 mole) at 0°–10° C. The mixture is then stirred for 30–60 minutes and the procedures outlined in Examples 2 and 3 are used to prepare dibenzoyl-t-butylhydrazine.

EXAMPLE 2

Preparation of t-Butyl hydrazine from N-chloro-t-Butylurea 55 mL of $H_2O$ and 9.47 g of NaOH (50%, 0.118 mole) are charged to 5-neck 500 mL RBF equipped with a thermometer and mechanical stirrer and cooled to 0°–10° C. The solid N-chloro-t-butylurea (5.4 g, 0.0358 mole) is added in portions over 45–60 min while maintaining the temperature at 0°–10° C. After stirring for 30–60 min, the NaCl is filtered off and washed with water. To the resulting filtrate at 25° C. is charged 37% HCl (ca. 12.3 g) until pH=2. After stirring for 1 hour, the crude aqueous solution is used directly in Example 3.

EXAMPLE 3

Preparation of Dibenzoyl-t-butylhydrazine from t-Butyl hydrazine

To the 4.3% aqueous solution of 4.47 g t-Butyl hydrazine from Example 2 (0.0358 mole) at pH 1.9° and 25° C. is charged 8.61 g NaOH (50%, 3 e.g., 0.107 mole) and about 80 mL $CH_2Cl_2$ resulting in a 2-phase mixture at pH 13–14. Benzoyl chloride (10.08 g, 2 eq., 0.107 mole) is then added drop-wise over 20 min at 25°–35° C., controlling for pH>9. After stirring at least 4 h, the mixture is transferred to a separatory funnel and the lower layer is drained off. After extracting the aqueous layer with about 25 mL $CH_2Cl_2$, the combined organic extracts are placed in a 5-neck 500 mL RBF and about ⅔ of the $CH_2Cl_2$ is stripped off. Heptane is then added over 45–60 min to precipitate the dibenzoyl-t-butylhydrazine. The resulting slurry is then stirred 1 h, filtered to obtain white flakes, and washed with heptane. After drying under vacuum, 9.1 g (86%) of white colored flakes are obtained (mp=174° C.).

EXAMPLE 4

Preparation of 2-benzoyl-1-tert-butyl-1-(3,4-dichlorobenzoyl)hydrazine

Benzoyl-2-tert-butylhydrazine (4.8 g, 0.025 mole) is stirred vigorously in a two-phase system of 50 mL of methylene chloride and 25 mL of 10% aqueous sodium hydroxide (2.5 g, 0.063 mole) until all dissolves. To this solution is added a solution of 3,4-dichlorobenzoyl chloride (7.3 g, 0.025 mole) in methylene chloride. After stirring the two-phase mixture several hours at ambient temperature, the solid is removed and washed with water and methylene chloride. Recrystallization from 2-propanol gives 7.1 g (78%) of product with mp 234°–235.5° C.

EXAMPLE 5

Preparation of 1-benzoyl-1-tert-butyl-2-(3,4-dichlorobenzoyl)hydrazine 3,4-Dichlorobenzoyl-2-tert-butylhydrazine (5.63 g, 0.0215 mole) is added to a rapidly stirring mixture of 40 mL of methylene chloride and 20 mL of 10% aqueous sodium hydroxide (2 g, 0.05 mole). Benzoyl chloride (d=1.211, 2.5 mL, 3.03 g, 0.0215 mole) in methylene chloride is added, and the reaction mixture stirred vigorously for approximately three hours at ambient temperature. The resulting solid is collected and washed with water and methylene chloride.

It should be understood that the instant specification and examples are set forth for illustration and not limitation, and that various modifications and changes may be made without departing from the spirit and scope of the present invention as defined in the appended claims.

I claim:

1. A method for the preparation of a t-butyl hydrazide or t-butyl hydrazine from a t-butyl urea starting product comprising the steps of:
   (a) halogenating the t-butyl urea starting product;
   (b) mixing the halogenated t-butyl urea with a dilute solution of an aqueous base;
   (c) adding a concentrated acid to the mixture produced by step (b) to produce a t-butyl hydrazine-containing dilute aqueous solution;
   (d) mixing an aqueous base, a first aprotic organic solvent, and an acid halide with the t-butyl hydrazine-containing dilute aqueous solution;
   (e) separating out the organic phase from the mixture produced by step (d); and
   (f) adding a second solvent to the organic phase of the mixture produced by step (e).

2. The method according to claim 1 wherein the hydrazide or hydrazine compound is acylated.

3. The method according to claim 2 wherein the acylated hydrazine compound is diacylated.

4. The method according to claim 3 wherein the diacylated hydrazine compound is a symmetrical compound.

5. The method according to claim 1 wherein the halogenated urea is a chlorinated urea.

6. The method according to claim 1 wherein about two molar equivalents of an acid halide are mixed with the t-butyl hydrazine-containing dilute aqueous solution to produce the hydrazine compound.

7. The method according to claim 1 wherein about one molar equivalent of an acid halide is mixed with the t-butyl hydrazine-containing dilute aqueous solution to produce the hydrazide compound.

8. The method according to claim 1 wherein the aqueous base is selected from the group consisting of $Na_2CO_3$, NaOH and KOH.

9. The method according to claim 1 wherein the concentrated acid is hydrochloric acid.

10. The method according to claim 1 wherein the t-butyl hydrazine-containing dilute aqueous solution has a concentration of between about 0.5 and 10%.

11. The method according to claim 10 wherein the concentration of the t-butyl hydrazine-containing dilute aqueous solution is between about 2 and 4%.

12. The method according to claim 1 wherein the first aprotic organic solvent is selected from the group consisting of methylene chloride, anhydrous tetrahydrofuran, ether and acetone.

13. The method according to claim 1 wherein the acid halide is selected from the group consisting of benzoyl chloride, acetyl chloride and benzenesulfonyl chloride.

14. The method according to claim 13 wherein the acid halide is benzoyl chloride.

15. The method according to claim 1 wherein the second solvent is heptane.

* * * * *